US010849864B2

(12) United States Patent
McHale et al.

(10) Patent No.: US 10,849,864 B2
(45) Date of Patent: Dec. 1, 2020

(54) COMBINATIONS AND METHODS FOR THE TREATMENT AND/OR PREVENTION OF FUNGAL INFECTIONS (71) Applicant: Novan, Inc., Morrisville, NC (US)

(72) Inventors: Kimberly McHale, Hillsborough, NC (US); Nathan Stasko, Chapel Hill, NC (US)

(73) Assignee: Novan, Inc., Morrisville, NC (US)

( * ) Notice: Subject to any disclaimer, the term of this patent is extended or adjusted under 35 U.S.C. 154(b) by 137 days.

(21) Appl. No.: 15/747,981

(22) PCT Filed: Jul. 25, 2016

(86) PCT No.: PCT/US2016/043880
§ 371 (c)(1),
(2) Date: Jan. 26, 2018

(87) PCT Pub. No.: WO2017/019614
PCT Pub. Date: Feb. 2, 2017

(65) Prior Publication Data
US 2018/0214392 A1 Aug. 2, 2018

Related U.S. Application Data (60) Provisional application No. 62/197,899, filed on Jul. 28, 2015.

(51) Int. Cl.
*A61K 31/137* (2006.01)
*A61K 31/655* (2006.01)
*A61K 31/695* (2006.01)
*A61P 31/10* (2006.01)
*A61K 41/00* (2020.01)
*C01B 21/24* (2006.01)
*A61K 45/06* (2006.01)
*A61K 31/795* (2006.01)
*A61K 31/80* (2006.01)
*A61K 33/00* (2006.01)

(52) U.S. Cl.
CPC .......... *A61K 31/137* (2013.01); *A61K 31/655* (2013.01); *A61K 31/695* (2013.01); *A61K 31/795* (2013.01); *A61K 31/80* (2013.01); *A61K 33/00* (2013.01); *A61K 41/0042* (2013.01); *A61K 45/06* (2013.01); *A61P 31/10* (2018.01); *C01B 21/24* (2013.01)

(58) Field of Classification Search
CPC .. A61K 33/00; A61K 41/0042; A61K 31/137; A61K 31/655; A61K 31/695; A61K 31/795; A61K 31/80; A61K 2300/00; C01B 21/24; C01B 21/203; C01B 21/20; A61P 31/10
See application file for complete search history.

(56) References Cited

U.S. PATENT DOCUMENTS

| 6,709,681 | B2 | 3/2004 | Benjamin et al. |
| 7,704,518 | B2 | 4/2010 | Tamarkin et al. |
| 8,114,442 | B2 | 2/2012 | Tucker et al. |
| 8,128,964 | B2 | 3/2012 | Tucker et al. |
| 8,241,650 | B2 | 8/2012 | Peters |
| 8,343,945 | B2 | 1/2013 | Tamarkin et al. |
| 8,362,091 | B2 | 1/2013 | Tamarkin et al. |
| 8,399,005 | B2 | 3/2013 | Schoenfisch et al. |
| 8,486,374 | B2 | 7/2013 | Tamarkin et al. |
| 8,591,876 | B2 | 11/2013 | Bauman et al. |
| 8,617,100 | B2 | 12/2013 | Eini et al. |
| 8,636,982 | B2 | 1/2014 | Tamarkin et al. |
| 8,795,635 | B2 | 8/2014 | Tamarkin et al. |
| 8,795,693 | B2 | 8/2014 | Tamarkin et al. |
| 8,900,553 | B2 | 12/2014 | Tamarkin et al. |
| 9,101,662 | B2 | 8/2015 | Tamarkin et al. |
| 9,161,916 | B2 | 10/2015 | Tamarkin et al. |
| 9,187,501 | B2 | 11/2015 | Schoenfisch et al. |
| 9,265,725 | B2 | 2/2016 | Tamarkin et al. |
| 9,320,705 | B2 | 4/2016 | Tamarkin et al. |
| 9,381,381 | B2 | 7/2016 | Benjamin |
| 9,427,605 | B2 | 8/2016 | Peters |
| 2004/0037897 | A1 | 2/2004 | Benjamin et al. |

(Continued)

FOREIGN PATENT DOCUMENTS

| CA | 2 594 407 A1 | 8/2006 |
| EP | 1 707 224 A1 | 10/2006 |

(Continued)

OTHER PUBLICATIONS

Axelgaard "AmGel Hydrogels" *Product Information*—http://www.alexgaard.com/Products/Hydrogels(3 pages) (2017).
Chow et al. "Formulation of Hydrophilic Non-Aqueous Gel: Drug Stability in Different Solvents and Rheological Behavior of Gel Matrices" *Pharmaceutical Research* 25(1):207-217 (2007).
Covidien "Hydrogels: The Industry's Choice in Gel" *Product Brochure* (4 pages) (2009).

(Continued)

*Primary Examiner* — Kortney L. Klinkel
(74) *Attorney, Agent, or Firm* — Myers Bigel, P.A.

(57) ABSTRACT

Provided are combinations comprising terbinafine or a pharmaceutically acceptable salt thereof and a NO source. The combination may be a synergistic combination. Also provided are methods of treating and/or preventing a fungal infection in a subject comprising administering terbinafine or a pharmaceutically acceptable salt thereof to the subject; and administering a NO source to the subject, thereby treating and/or preventing the fungal infection in the subject. The dose of terbinafine or a pharmaceutically acceptable salt thereof and the dose of the NO source administered to the subject may achieve a synergistic effect.

17 Claims, 4 Drawing Sheets

(56) References Cited

U.S. PATENT DOCUMENTS

| | | |
|---|---|---|
| 2004/0105898 A1 | 6/2004 | Benjamin et al. |
| 2005/0037093 A1 | 2/2005 | Benjamin |
| 2005/0038473 A1 | 2/2005 | Tamarkin et al. |
| 2005/0232869 A1 | 10/2005 | Tamarkin et al. |
| 2005/0271596 A1 | 12/2005 | Friedman et al. |
| 2006/0269620 A1 | 11/2006 | Morris et al. |
| 2006/0275218 A1 | 12/2006 | Tamarkin et al. |
| 2007/0286840 A1* | 12/2007 | Arnold ............... A61K 31/655 424/78.35 |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0044444 A1 | 2/2008 | Tamarkin et al. |
| 2008/0063607 A1 | 3/2008 | Tamarkin et al. |
| 2008/0069779 A1 | 3/2008 | Tamarkin et al. |
| 2008/0138296 A1 | 6/2008 | Tamarkin et al. |
| 2008/0152596 A1 | 6/2008 | Friedman et al. |
| 2008/0166303 A1 | 7/2008 | Tamarkin et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0130029 A1 | 5/2009 | Tamarkin et al. |
| 2009/0175799 A1 | 7/2009 | Tamarkin et al. |
| 2009/0214618 A1 | 8/2009 | Schoenfisch et al. |
| 2010/0015253 A1 | 1/2010 | Benjamin |
| 2010/0098733 A1 | 4/2010 | Stasko |
| 2010/0129474 A1 | 5/2010 | Benjamin et al. |
| 2010/0152683 A1 | 6/2010 | Lindgren et al. |
| 2010/0221195 A1 | 9/2010 | Tamarkin et al. |
| 2010/0239512 A1 | 9/2010 | Morris et al. |
| 2010/0266510 A1 | 10/2010 | Tamarkin et al. |
| 2010/0310476 A1 | 12/2010 | Tamarkin et al. |
| 2010/0331968 A1 | 12/2010 | Morris et al. |
| 2011/0045037 A1 | 2/2011 | Tamarkin et al. |
| 2011/0052650 A1 | 3/2011 | Morris et al. |
| 2011/0086234 A1 | 4/2011 | Stasko et al. |
| 2011/0097279 A1 | 4/2011 | Tamarkin et al. |
| 2011/0212033 A1 | 9/2011 | Tamarkin et al. |
| 2012/0134951 A1 | 5/2012 | Stasko et al. |
| 2012/0141384 A1 | 6/2012 | Tamarkin et al. |
| 2012/0237453 A1 | 9/2012 | Tamarkin et al. |
| 2012/0295952 A1 | 11/2012 | Collard et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2014/0004176 A1 | 1/2014 | Fossel et al. |
| 2014/0105986 A1 | 4/2014 | Doxey et al. |
| 2014/0134321 A1 | 5/2014 | Stasko et al. |
| 2014/0171395 A1 | 6/2014 | Schoenfisch et al. |
| 2014/0193502 A1 | 7/2014 | Tamarkin et al. |
| 2014/0221331 A1 | 8/2014 | Barraud et al. |
| 2014/0248219 A1 | 9/2014 | Tamarkin et al. |
| 2014/0255318 A1 | 9/2014 | Stasko et al. |
| 2014/0271494 A1 | 9/2014 | Tamarkin et al. |
| 2015/0010656 A1 | 1/2015 | Perricone |
| 2015/0017103 A1 | 1/2015 | Tamarkin et al. |
| 2015/0025060 A1 | 1/2015 | Tamarkin et al. |
| 2015/0111973 A1 | 4/2015 | Bauman et al. |
| 2015/0118164 A1 | 4/2015 | Tamarkin et al. |
| 2015/0157729 A1 | 6/2015 | Petersson et al. |
| 2015/0225488 A1 | 8/2015 | Schoenfisch et al. |
| 2016/0008275 A1 | 1/2016 | Doxey et al. |
| 2016/0199295 A1 | 7/2016 | Doxey et al. |
| 2016/0256484 A1 | 9/2016 | Doxey et al. |
| 2017/0196905 A1 | 7/2017 | Doxey et al. |
| 2018/0200541 A1 | 7/2018 | Doxey et al. |

FOREIGN PATENT DOCUMENTS

| | | |
|---|---|---|
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| WO | WO 2005/004984 A1 | 1/2005 |
| WO | WO 2006/084910 A2 | 8/2006 |
| WO | WO 2006/084912 A1 | 8/2006 |
| WO | WO 2006/100154 A1 | 9/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2010/044875 A2 | 4/2010 |
| WO | WO 2011/022652 A1 | 2/2011 |
| WO | WO 2011/022680 A2 | 2/2011 |
| WO | WO 2011/047013 A1 | 4/2011 |
| WO | 2012078649 | 6/2012 |
| WO | WO 2012/082976 A1 | 6/2012 |
| WO | WO 2012/100174 A1 | 7/2012 |
| WO | WO 2012/118819 A2 | 9/2012 |
| WO | WO 2012/118829 A2 | 9/2012 |
| WO | WO 2012/155203 A1 | 11/2012 |
| WO | WO 2013/006608 A1 | 1/2013 |
| WO | WO 2013/006613 A1 | 1/2013 |
| WO | WO 2013/029009 A1 | 2/2013 |
| WO | WO 2013/063354 A1 | 5/2013 |
| WO | WO 2013/138073 A1 | 9/2013 |
| WO | WO 2013/138075 A1 | 9/2013 |
| WO | WO 2014/028847 A1 | 2/2014 |
| WO | WO 2014/134502 A1 | 9/2014 |
| WO | WO 2015/021382 A2 | 2/2015 |
| WO | WO 2016/010988 A1 | 1/2016 |
| WO | WO 2016/022170 A1 | 2/2016 |
| WO | WO 2016/160089 A1 | 10/2016 |
| WO | WO 2017/011031 A1 | 1/2017 |

OTHER PUBLICATIONS

De Groote et al. "NO Inhibitions: Antimicrobial Properties of Nitric Oxide" *Clinical Infectious Diseases* 21(Suppl. 2):S162-S165 (1995).

Finnen et al. "Topical application of acidified nitrite to the nail renders it antifungal and causes nitrosation of cysteine groups in the nail plate" *British Journal of Dermatology* 157:494-500 (2007).

International Search Report and the Written Opinion of the International Searching Authority corresponding to International Patent Application No. PCT/US2016/043880 (10 pages) (dated Oct. 4, 2016).

McHale et al. "In Vitro and In Vivo Nail Penetration of Nitric Oxide Releasing Formulations for the Topical Treatment of Onychomycosis" *Abstract*—www.novantherapeutics.com (1 page) (2016).

McHale et al. "In Vitro Nail Penetration of Nitric Oxide-releasing Formulations for the Topical Treatment of Onychomycosis" *Microbe Poster*—www.novantherapeutics.com (1 page) (2016).

Novan, Inc. Press Release "Novan Announces First Patient Dosed in Phase 2 Anti-Fungal Program" http://investors.novan.com (4 pages) (Jul. 21, 2016).

(56) References Cited

OTHER PUBLICATIONS

Kai et al. "Management of Acral Lentiginous Melanoma" https://www.intechopen.com/books/melanoma-from-early-detection-to-treatment/management-of-acral-lentiginous-melanoma (6 pages total; no pagination) (2013).

* cited by examiner

COMBINATIONS AND METHODS FOR THE TREATMENT AND/OR PREVENTION OF FUNGAL INFECTIONS

RELATED APPLICATIONS

This application claims the benefit of and priority to U.S. Provisional Application Ser. No. 62/197,899 filed on Jul. 28, 2015, the disclosure of which is hereby incorporated by reference herein in its entirety.

FIELD

The present invention relates generally to combinations and methods for treating and/or preventing fungal infections.

BACKGROUND

Fungi can be difficult to kill. Accordingly, fungal infections of the skin and/or nail can be difficult to treat and reoccurrence can be common. While different medications exist to treat fungal infections, serious side effects (e.g., liver damage) may occur and a patient may develop resistance to one or more drugs used to treat fungal infections. For example, azoles are a class of five-membered heterocyclic ring compounds containing at least one nitrogen atom. Azoles are concentration-independent fungistatic agents and work by inhibiting the fungal enzyme cytochrome p450 lanosterol 14α-demethylase, which is important for ergosterol production. However, resistance can develop to azoles and resistance to one azole generally confers resistance to the whole class of azole drug compounds. Terbinafine is another drug compound that may be used to treat a fungal infection and works in a different manner than azoles as terbinafine inhibits squalene epoxidase in the pathway for producing ergosterol.

The present invention may address previous shortcomings in the art by providing combinations and/or methods for treating and/or preventing fungal infections.

SUMMARY

It is noted that aspects described with respect to one embodiment may be incorporated in different embodiments although not specifically described relative thereto. Some embodiments are directed to combinations and/or methods for treating and/or preventing a fungal infection. In some embodiments, a method of treating and/or preventing a fungal infection in a subject in need thereof includes administering and/or using a combination described herein.

Some embodiments include a method of treating and/or preventing a fungal infection in a subject, the method comprising: administering terbinafine or a pharmaceutically acceptable salt thereof to the subject; and administering a NO source to the subject, thereby treating and/or preventing the fungal infection in the subject.

Provided according to some embodiments is a combination comprising terbinafine or a pharmaceutically acceptable salt thereof and a NO source.

Further provided according to some embodiments is a kit comprising terbinafine or a pharmaceutically acceptable salt thereof and a NO source. In some embodiments, terbinafine or a pharmaceutically acceptable salt thereof and the NO source are separately stored.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, ±10%, ±5%, ±1%, ±0.5%, or even ±0.1% of the specified value, as well as the specified value. For example, "about X" where X is the measurable value, is meant to include X as well as variations off 20%, ±10%, +5%, ±1%, ±0.5%, or even ±0.1% of X. A range provided herein for a measureable value may include any other range and/or individual value therein.

Provided according to embodiments of the present invention are combinations useful for treating and/or preventing a fungal infection. According to some embodiments of the present invention, provided is a combination comprising terbinafine or a pharmaceutically acceptable salt thereof and a nitric oxide (NO) source. Thus, combinations of the present invention comprise at least two active ingredients (i.e., terbinafine or a pharmaceutically acceptable salt thereof and a NO source) and may be a pharmaceutical combination.

A "nitric oxide source", "NO source", and grammatical variants thereof as described herein refer to nitric oxide in any form and/or nitric oxide provided and/or supplied in any way and/or by any means. For example, a NO source may be gaseous nitric oxide, a nitric oxide-releasing active pharmaceutical ingredient ("NO-releasing API") as defined herein, and/or an active pharmaceutical ingredient (API) and/or therapy that stimulates and/or increases the endogenous release and/or availability of nitric oxide. Thus, a NO source may be an agent (e.g., an active pharmaceutical ingredient) and/or therapy that stores, releases, liberates, provides, and/or supplies nitric oxide and/or nitric oxide alone (i.e., nitric oxide alone in gaseous form,

).

One or more (e.g., 1, 2, 3, 4, 5, or more) different NO sources may be used in a combination and/or method of the present invention.

Some embodiments include administering a NO source to a subject such that nitric oxide is administered to the subject, optionally to the skin and/or nail of the subject. In some embodiments, administration of a NO source to a subject may increase a level or concentration of nitric oxide at a given site on and/or in a subject. In some embodiments, administering a NO source may locally increase a level or concentration of nitric oxide at a desired site on and/or in a subject. In some embodiments, a NO source may increase a level or concentration of nitric oxide in the skin and/or a nail of a subject where a fungal infection is present. In some embodiments, a level or concentration of nitric oxide at a given site on and/or in a subject may be increased by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, or more compared to a level or concentration of nitric oxide at a given site on and/or in a subject in the absence of a NO source, combination, and/or method of the present invention.

In some embodiments, a NO source may comprise gaseous nitric oxide that is administered directly to the skin and/or nail of a subject (i.e., nitric oxide that is administered in gaseous form without the aid of an agent). In some embodiments, a NO source may comprise an API (e.g., an NO-releasing API) that is administered to a subject in any manner (e.g., orally, topically, etc.). In some embodiments, a NO source may be administered directly to the subject and/or administered to the subjected together with one or more excipients (e.g., in a composition comprising the API, such as a topical composition comprising the API, and/or in an oral dosage form comprising the API). In some embodiments, a NO source may comprise a NO-releasing API. Thus, administration of the API (e.g., an NO-releasing API) to a subject may increase a level or concentration of nitric oxide at a given site on and/or in a subject, such as the skin and/or a nail of the subject. In some embodiments, the NO source may comprise acidified nitrite. In some embodiments, the NO source may be an API that stimulates and/or increases the endogenous release and/or availability of nitric oxide. In some embodiments, the NO source may comprise a therapy that stimulates and/or increases the endogenous release and/or availability of nitric oxide. In some embodiments, the skin and/or a nail of a subject may be exposed to light that releases nitric oxide from endogenous stores of nitric oxide in the subject.

In some embodiments, a therapy that stimulates and/or increases the endogenous release and/or availability of nitric oxide in a subject may comprise exposing the subject to light and/or an electrical current. For example, in some embodiments, administering a NO source may comprise exposing a subject to light and/or electrical current that stimulates the release of nitric oxide from endogenous stores in the subject and/or increases the availability of nitric oxide from endogenous stores in the subject.

In some embodiments, a NO source may be administered to a subject and then the release of nitric oxide from the NO source may be stimulated, increased, and/or initiated. For example, in some embodiments, upon administering a NO source to a subject, nitric oxide may be released from the NO source by exposing the subject and/or the NO source to light and/or an electrical current. In some embodiments, the portion of the subject to which the NO source is in contact with may be exposed to light and/or the electrical current.

Exposing the subject or a portion thereof (e.g., the skin and/or a nail of the subject) and/or a NO source to a light that stimulates, liberates, and/or releases nitric oxide, such as from endogenous stores of nitric oxide in the subject and/or from the NO source, may comprise exposing the subject or a portion thereof and/or the NO source to one or more wavelengths of light. In some embodiments, the subject or a portion thereof and/or the NO source may be exposed to light with a wavelength in a range of about 400 nm and about 500 nm. In some embodiments, the portion of the subject to which the NO source is administered and/or in contact with is exposed to light. In some embodiments, the NO source comprises copper and sodium nitrite, and administering the NO source to the subject comprises releasing nitric oxide from the NO source by application of light having a wavelength of between about 400 nm and about 500 nm.

In some embodiments, an electrical current is applied to a subject or a portion thereof (e.g., the skin and/or a nail of the subject) and/or a NO source in an amount sufficient to stimulate, liberate, and/or release nitric oxide, such as from endogenous stores of nitric oxide in the subject and/or from the NO source. In some embodiments, the NO source comprises sodium nitrite and nitric oxide is released from the NO source by application of an electrical current to the NO source. In some embodiments, application of the electrical current includes at least one copper containing electrode.

It was discovered that terbinafine or a pharmaceutically acceptable salt thereof and a NO source are compatible with each other such that the combination of terbinafine and the NO source can enhance the anti-fungal effects of terbinafine and/or the NO source individually. In some embodiments, a combination comprising terbinafine or a pharmaceutically acceptable salt thereof and a NO source can be additive (i.e., the effect of the two active ingredients is equal to the sum of the effect of the two active ingredients taken separately). Furthermore, it was unexpectedly discovered that a combination comprising terbinafine or a pharmaceutically acceptable salt thereof and a NO source can be synergistic.

The term "pharmaceutically acceptable salt" refers to a salt or salts prepared from at least one pharmaceutically acceptable non-toxic acid or base including inorganic acids and bases, and organic acids and bases. Pharmaceutically acceptable salts of compounds according to embodiments of the invention include the acid addition and base salts thereof, and may be made using techniques known in the art, such as, but not limited to, reacting the compound with the desired base or acid. Suitable pharmaceutically acceptable base addition salts for compounds according to embodiments of the present invention include metallic salts (e.g., alkali metal salts and/or alkaline earth metal salts) made from aluminum, calcium, lithium, magnesium, potassium, sodium, and zinc; or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include xinofoate, hydrochloride mesylate, zinc, potassium, or iron salts. In certain embodiments, both water-soluble and water-insoluble salts will be useful based on the mode of administration.

"Synergistic", "synergy", or grammatical variants thereof as used herein refer to a combination exhibiting an effect greater than the effect that would be expected from the sum of the effects of the individual active ingredients of the combination alone. For example, the terms "synergistic" or "synergy" with regard to a combination of terbinafine or a pharmaceutically acceptable salt thereof and a NO source (for example, in the form of a single unit dosage form or a kit as described herein) for treating and/or preventing a fungal infection refers to an efficacy for the treatment and/or prevention of the fungal infection that is greater than that which would be expected from the sum of the individual effects of terbinafine or a pharmaceutically acceptable salt thereof and a NO source alone.

A synergistic combination of the present invention may provide one or more of the following advantages: enhanced efficacy compared to each of the active ingredients when used alone, lowering the required dose of one or more of the active ingredients of the combination, reducing the side effects of one or more of the active ingredients of the combination, and/or rendering one or more of the active ingredients more tolerable to a subject in need of treatment and/or prevention of a fungal infection. "Enhanced" as used herein in reference to efficacy refers to any improvement in producing the desired effect or result. In some embodiments, a combination of the present invention may enhance efficacy by increasing efficacy (e.g., increasing the extent or amount of a desired result) compared to the efficacy achieved by at least one of the active ingredients of the combination alone. As one skilled in the art will recognize, an increase in efficacy may be a decrease or reduction in a clinical symptom associated with a fungal infection, such as, for example, a decrease in itching and/or a decrease in the size of a lesion. In some embodiments, a combination of the present invention provides and/or allows for a lower dose of both terbinafine or a pharmaceutically acceptable salt thereof and a NO source, and/or may provide the same and/or an increased therapeutic and/or prophylactic effect compared to the therapeutic and/or prophylactic effect achieved with one or more of the active ingredients alone.

Synergy or a synergistic effect can be calculated using methods known to those of skill in the art. For example, using suitable methods including, but not limited to, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In some embodiments, synergy or a synergistic effect may be determined using the "checkerboard" technique, which looks at inhibition of bacterial growth. For example, using the checkerboard technique, the Minimum Inhibitory Concentration (MIC) for each active ingredient alone may determined. Then, the MIC for the active ingredients when used together may be determined. The Fractional Inhibitory Concentration (FIC) is determined for each active ingredient and is calculated using the following equation FIC=[Concentration of active ingredient when used together]/[Concentration of active ingredient alone]. The FIC for each active ingredient is then added to achieve the Fractional Inhibitory Index (FIX), with the FIX value providing the following indications: FIX≤0.5 indicates a synergistic effect, 0.5<FIX≤1 indicates an additive effect; 1<FIX≤4 indicates indifference, and 4>indicates an antagonistic effect.

Alternatively or in addition, the "time kill" technique, which looks at bacterial killing during a given amount of time (e.g., 3, 6, 24, or 48 hours), could be used to determine synergy or a synergistic effect. Using the time kill technique, a combination may be synergistic when the combination provides a greater than or equal to 2 $\log_{10}$ (CFU/mL) decrease in fungi compared to a single active ingredient that is the most effective in killing the fungus.

The term "combination" as used to herein refers to a fixed combination or a non-fixed combination, both of which provide and/or are suitable for the combined administration of the at least two active ingredients (i.e., terbinafine or a pharmaceutically acceptable salt thereof and a NO source).

In some embodiments, a combination may show and/or provide an additive or synergistic effect, such as, for example, upon administration to a subject, and thus may be an additive or synergistic combination, respectively. In some embodiments, the concentration or amount of each active ingredient (e.g., terbinafine or a pharmaceutically acceptable salt thereof and a NO source) in the combination may be a concentration or amount that can achieve an additive or synergistic effect upon administration to a subject. Thus, administering a combination of the present invention may provide a dose of terbinafine or a pharmaceutically acceptable salt thereof and a NO source that achieves an additive or synergistic effect.

The term "fixed combination" or "single unit dosage form" as used herein refer to a single entity (e.g., a single carrier or vehicle) that contains the at least two active ingredients (i.e., terbinafine or a pharmaceutically acceptable salt thereof and a NO source). A fixed combination may also be referred to as a single formulation and/or a single composition that comprises the at least two active ingredients. Thus, a fixed combination can provide and/or deliver an amount of both of the two or more active ingredients, such as, for example, upon administration of the combination to a subject. A fixed combination may be designed to deliver to a subject an amount of each of the at least two active ingredients along with any pharmaceutically acceptable carriers and/or excipients. Accordingly, administration of a fixed combination provides for the simultaneous administration of the at least two active ingredients to a subject. In some embodiments, a fixed combination may be a tablet, capsule, pill, patch, and/or topical composition (e.g., a gel, ointment, foam, etc.). In some embodiments, administration of a fixed combination provides and/or delivers an amount of each of the at least two active ingredients that is jointly therapeutically and/or prophylactically effective for the treatment and/or prevention of a fungal infection. In some embodiments, administration of a fixed combination of the present invention provides an additive or synergistic effect.

In some embodiments, terbinafine or a pharmaceutically acceptable salt thereof and a NO source are in a single unit dosage form. In some embodiments, the single unit dosage form may comprise an NO-releasing active pharmaceutical ingredient. In some embodiments of the present invention, a topical composition (e.g., a gel, ointment, cream, foam, or spray) comprising terbinafine or a pharmaceutically acceptable salt thereof and an NO-releasing active pharmaceutical ingredient may be provided.

The term "non-fixed combination", "separate dosage forms", or "kit" refers to at least two separate entities (e.g., two separate dosage forms) and/or therapies, where one of the at least two separate entities and/or therapies comprises terbinafine or a pharmaceutically acceptable salt thereof and the other of the at least two separate entities and/or therapies comprises a NO source. Thus, a non-fixed combination may include at least two separate formulations and/or compositions that may or may not be formulated for delivery by the same route (e.g., oral, topical, parenteral, etc.). Administration of a non-fixed combination may separately provide and/or deliver an amount of each of the at least two active ingredients along with any pharmaceutically acceptable carriers and/or may separately store the at least two active ingredients. In some embodiments, a non-fixed combination may separately store the at least two active ingredients (i.e., terbinafine or a pharmaceutically acceptable salt thereof and a NO source), but the at least two separate entities and/or therapies comprising the at least two active ingredients may be combined (e.g., mixed together) prior to administration so that they are simultaneously administered.

In some embodiments, a non-fixed combination may comprise terbinafine or a pharmaceutically acceptable salt thereof and/or a NO source in a form for oral administration or topical administration. In some embodiments, terbinafine or a pharmaceutically acceptable salt thereof may be formulated for oral administration (e.g., a tablet, pill, or liquid) or topical administration (e.g., a cream, spray, or powder) to a subject and a NO source may be formulated for topical administration.

Example dosage forms including terbinafine or a pharmaceutically acceptable salt thereof are known in the art and include, but are not limited to, those commercially available under the trade name Lamisil$^{AT}$®, Lamisil$^{AF}$®, and Terbinex™. Example dosage forms for administering a NO source comprising a NO-releasing API include, but are not limited to, those described in International Application Nos. PCT/US2015/040319 and PCT/US2015/039908, and International Application Publication Nos. WO 2013/006608, WO 2013/138075, and WO 2014/134502, the contents of each of which is incorporated herein by reference in its entirety.

A non-fixed combination may provide for the simultaneous or sequential administration of the at least two active ingredients. In some embodiments, the separate entities and/or therapies of a non-fixed combination may be administered to a subject either simultaneously or sequentially in any order, optionally with no specific time limits. In some embodiments, the time intervals for sequential administration of the two or more separate entities and/or therapies are such that an additive or synergistic effect may be achieved due to administration of the combination.

In some embodiments, a non-fixed combination may comprise terbinafine or a pharmaceutically acceptable salt thereof and a medical device that can generate, stimulate, liberate, and/or release nitric oxide to a subject or a portion thereof, such as to the skin and/or a nail of the subject. The medical device may locally generate, stimulate, liberate, and/or release nitric oxide to a subject or a portion thereof. Example medical devices include, but are not limited to, a phototherapy device, such as a phototherapy device that can generate nitric oxide in the skin and/or nail of a subject.

In some embodiments, a kit may be provided comprising terbinafine or a pharmaceutically acceptable salt thereof and a NO source. The kit may separately store terbinafine or a pharmaceutically acceptable salt thereof and a NO source. In some embodiments, the kit may be configured to mix, combine, or the like terbinafine or a pharmaceutically acceptable salt thereof and a NO source upon dispensing and/or for application to the skin and/or nail of a subject in a desired ratio (e.g., 1:1, 2:1, etc.).

According to some embodiments, a combination of the present invention may separately store and/or administer terbinafine or a pharmaceutically acceptable salt thereof and a NO source. A combination of the present invention may be for simultaneous, separate, and/or sequential use. In some embodiments, administration of a combination of the present invention may simultaneously administer the at least two active ingredients to a subject either in the same dosage form or in separate dosage forms. In some embodiments, administration of a combination of the present invention may sequentially administer the at least two active ingredients to a subject, optionally in any order.

In some embodiments of the present invention, terbinafine or a pharmaceutically acceptable salt thereof and a NO source may be simultaneously administered to a subject either in the same dosage form or in separate dosage forms. In some embodiments, terbinafine or a pharmaceutically acceptable salt thereof and a NO source may be sequentially administered to a subject, optionally in any order. The administration of terbinafine or a pharmaceutically acceptable salt thereof and a NO source to a subject may provide an additive or synergistic effect.

A combination may comprise a NO source in the form of gaseous nitric oxide. In some embodiments, gaseous nitric oxide is provided in the absence of an agent, such as a NO-releasing API. Gaseous nitric oxide may be administered directly or indirectly to the skin and/or nail of a subject. Applying nitric oxide "directly" refers to applying gaseous nitric oxide to the surface of the skin and/or nail, without any barriers between the gas flow and the skin and/or nail. Applying the gaseous nitric oxide "indirectly" refers to application of gaseous nitric oxide through a substrate, such as a cloth, dressing, membrane, medicament, powder, ointment and the like, prior to reaching the skin and/or nail.

Gaseous nitric oxide may be applied to the skin and/or nail at any suitable pressure, flow rate, and/or concentration, and may be applied for any suitable length of time. It may be applied in a sealed system (e.g., a mask or chamber affixed over the affected area) or it may be freely flowed over the surface of the skin and/or nail. The gaseous nitric oxide may also be present in a mixture of gases, or may be applied by itself.

In some embodiments, a NO source may comprise a nitric oxide-releasing active pharmaceutical ingredient (NO-releasing API). Thus, a combination of the present invention may comprise a NO-releasing API. "Nitric oxide releasing active pharmaceutical ingredient" and "NO-releasing API," as used herein, refer to a compound or composition that stores and/or releases nitric oxide. Thus, an NO-releasing API is not in the form of gaseous nitric oxide, but instead stores and/or releases nitric oxide such that nitric oxide may be provided to the skin and/or nail of a subject upon administration. In some embodiments, the NO-releasing API comprises acidified nitrite. In some embodiments, the NO-releasing API includes a nitric oxide-releasing compound, hereinafter referred to as a "NO-releasing compound." An NO-releasing compound includes at least one NO donor, which is a functional group that may release nitric oxide under certain conditions.

Any suitable NO-releasing compound may be used. In some embodiments, the NO-releasing compound includes a small molecule compound that includes an NO donor group. "Small molecule compound" as used herein is defined as a compound having a molecular weight of less than 500 daltons, and includes organic and/or inorganic small molecule compounds. In some embodiments, the NO-releasing compound includes a macromolecule that includes an NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 µm and may comprise the aggregation of two or more macromolecules, whereby the macromolecular structure is further modified with an NO donor group.

In some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxyl amine and hydroxyurea. Any suitable combination of NO donors and/or NO-releasing compounds may also be used in a second composition as described herein. Additionally, the NO donor may be incorporated into or onto the small molecule or macromolecule through covalent and/or non-covalent interactions.

An NO-releasing macromolecule may be in the form of an NO-releasing particle, such as those described in U.S. Pat. Nos. 8,282,967, 8,962,029 or 8,956,658, the disclosures of which are incorporated by reference herein in their entirety. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in International Application No. PCT/US2012/052350 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

As an example, in some embodiments of the present invention, a nitric oxide-releasing active pharmaceutical ingredient may include NO-loaded precipitated silica. The NO-loaded precipitated silica may be formed from nitric oxide donor modified silane monomers into a co-condensed siloxane network. In one embodiment of the present invention, the nitric oxide donor may be an N-diazeniumdiolate. In some embodiments of the present invention, the nitric oxide-releasing active pharmaceutical ingredient may comprise, consist essentially of, or consist of a co-condensed siloxane network comprising a diazeniumdiolate (e.g., a N-diazeniumdiolate).

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors. In some embodiments of the present invention, the nitric oxide-releasing active pharmaceutical ingredient may comprise, consist essentially of, or consist of a co-condensed silica network synthesized from the condensation of a silane mixture comprising an alkoxysilane and at least one aminoalkoxysilane having an amine substituted by a diazeniumdiolate (e.g., a N-diazeniumdiolate).

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula Si(OR)4, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: R"—(NH—R')n-Si(OR)3, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl) phenethyltrimethoxysilane (AEMP3); [3-(methylamino)propyl]trimethoxysilane (MAP3); N-butylaminopropyltrimethoxysilane(n-BAP3); t-butylaminopropyltrimethoxysilane(t-BAP3);N-ethylaminoisobutyltrimethoxysilane(EAiB3); N-phenylamino-propyltrimethoxysilane (PAP3); and N-cyclohexylaminopropyltrimethoxysilane (cHAP3).

In some embodiments, the aminoalkoxysilane has the formula: NH [R'—Si(OR)3]2, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl) propyl] ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: R"—N(NONO—X+)—R'—Si(OR)3, wherein R is alkyl, R' is alkylene or aralkylene, R" is alkyl or alkylamine, and X+ is a cation selected from the group consisting of Na+, K+ and Li+.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In another embodiment, the amino group of aminoalkoxysilane is substituted with a diazeniumdiolate, and the aminoalkoxysilane having a formula of R"—N(NONO—X+)—R'—Si(OR)3, wherein: R is alkyl, R' is alkylene or aralkylene, R" is alkyl or alkylamine, and X+ is a cation selected from the group consisting of Na+ and K+.

In certain embodiments, the NO-releasing API may comprise a co-condensed silica network comprising diazeniumdiolated aminoethylaminopropyl trimethoxy silane (AEAP3) and tetra methyl orthosilicate (TMOS) and/or a co-condensed silica network comprising diazeniumdiolated aminoethylaminopropyl trimethoxy silane (AEAP3) and tetraethyl orthosilicate (TEOS). In some embodiments, the NO-releasing API may comprise a co-condensed silica network comprising diazeniumdiolated methylaminopropyl trimethoxysilane (MAP3) and tetra methyl orthosilicate (TMOS) and/or a co-condensed silica network comprising diazeniumdiolated methylaminopropyl trimethoxysilane (MAP3) and tetraethyl orthosilicate (TEOS).

In some embodiments of the invention, the particle size of a NO-releasing API may be in a range of about 20 nm to about 20 µM or any range therein, such as, but not limited to, about 100 nm to about 20 µm or about 1 µm to about 20 µm. The particle size may be tailored to minimize or prevent toxicity and/or penetration through the epidermis (or compromised dermis) and into the blood vessels. In some embodiments, the particle size is distributed around a mean particle size of less than 20 µm, or any range therein, and the size may allow the particle to enter a follicle. In some embodiments, a NO-releasing API may have a particle size that is distributed around a mean particle size of about 20, 19, 18, 17, 16, 15, 14, 13, 12, 11, 10, 9, 8, 7, 6, 5, 4, 3, 2, or 1 µm. In further embodiments, a NO-releasing API may have a particle size that is distributed around a mean particle size of less than 10 µm, or any range therein, such as, but not limited to about 2 µm to about 10 µm or about 4 µm to about 8 µm. In other embodiments, the particle size may be distributed around a mean particle size of greater than 20 µm, or any range therein, and the size may prevent the particle from entering the follicle. In still further embodiments, a mixture of particles with mean particle sizes distributed around two or more mean particle sizes may be provided. A NO-releasing API may be micronized (e.g., ball and/or jet milled). Methods for providing a desired particle size and/or micronization include, but are not limited to, those described in U.S. Patent Application Publication No. 2013/0310533, which is incorporated herein by reference in its entirety.

In some embodiments, a combination and/or method of the present invention provides and/or delivers nitric oxide to the skin and/or nail of a subject in a concentration effective to inhibit fungi growth and/or kill fungi. In some embodiments, a combination and/or method of the present invention provides and/or delivers nitric oxide to the skin and/or nail of a subject in an amount that is equal to or less the concentration effective to inhibit fungi growth and/or kill fungi for a NO source alone ("effective concentration for the NO source alone"). In some embodiments, a combination and/or method of the present invention provides and/or delivers nitric oxide to the skin and/or nail of a subject in an amount that is equal to or less than the minimum inhibitory concentration (MIC) for a NO source alone as determined for a fungus, such as, for example, Trichophyton rubrum. The concentration of nitric oxide that is provided and/or delivered to the skin and/or nail of a subject may be at least 5%, 10%, 15%, 20%, 25%, 30%, 35%, 40%, 45%, 50%, 55%, 60%, 65%, 70%, 75%, 80%, 85%, 90%, or 95% less than the effective concentration for the NO source alone and/or the MIC for nitric oxide alone as determined for a fungus. In some embodiments, the concentration of nitric oxide that is provided and/or delivered to the skin and/or nail of a subject may be at least 1.5-fold (e.g., 2, 2.5, 3, 3.5, 4, 4.5, 5, 5.5, or 6-fold) less than the effective concentration for the NO source alone and/or the MIC for nitric oxide alone as determined for a fungus.

In some embodiments, a combination and/or method of the present invention may comprise an NO-releasing API that provides and/or delivers nitric oxide to the skin and/or nail of a subject. In some embodiments, the combination may comprise a composition, such as a composition for topical administration that may topically deliver nitric oxide to the skin and/or nail of a subject. In some embodiments, the combination may comprise a composition that comprises the NO-releasing API. The composition may comprise an NO-releasing API in an amount of about 0.5% to about 70% by weight of the composition. For example, in some embodiments, a NO-releasing API may be present in a composition in an amount of about 0.5% to about 20%, about 0.5% to about 5%, about 1% to about 20%, about 1% to about 10%, about 1% to about 8%, about 1% to about 20%, about 5% to about 15%, about 1% to about 70%, about 1% to about 50%, or about 2% to about 6% by weight of the composition. In certain embodiments, a nitric oxide-releasing active pharmaceutical ingredient may be present in a composition of the present invention in an amount of about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% by weight of the composition.

A composition of the present invention may comprise a NO-releasing API and may store and/or release nitric oxide in an amount of about 0.05% to about 20% by weight of the composition, such as, but not limited to, about 0.15% to about 2%, about 0.15% to about 1%, about 0.3% to about 1.2%, about 0.15% to about 6%, about 1% to about 10%, about 3% to about 6%, about 2% to about 20%, about 5% to about 15%, about 10% to about 20%, or about 1% to about 5% by weight of the composition. In certain embodiments, a composition of the present invention may comprise a NO-releasing API and may store and/or release NO in an amount of about 0.15%, 0.3%, 0.6%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, or 20% by weight of the composition. The amount of nitric oxide released from a composition may be determined using real time in vitro release testing. In some embodiments, nitric oxide release may be determined using a chemiluminescent nitric oxide analyzer.

In some embodiments, a combination and/or method of the present invention provides and/or delivers terbinafine or a pharmaceutically acceptable salt thereof to the skin and/or nail of a subject in a concentration effective to inhibit fungi growth and/or kill fungi. In some embodiments, a combination and/or method of the present invention provides and/or delivers terbinafine or a pharmaceutically acceptable salt thereof to the skin and/or nail of a subject in an amount that is equal to or less the concentration effective to inhibit fungi growth and/or kill fungi for terbinafine or a pharmaceutically acceptable salt thereof alone ("effective concentration for terbinafine alone"). In some embodiments, a combination and/or method of the present invention provides and/or delivers terbinafine or a pharmaceutically acceptable salt thereof to the skin and/or nail of a subject in an amount that is equal to or less than the minimum inhibitory concentration (MIC) for terbinafine or a pharmaceutically acceptable salt thereof alone as determined for a fungus, such as, for example, *T. rubrum*. The concentration of terbinafine or a pharmaceutically acceptable salt thereof that is provided and/or delivered to the skin and/or nail of a subject may be at least 5%, 10%, 15%, 20%, 25%, 30%, 35%, 40%, 45%, 50%, 55%, 60%, 65%, 70%, 75%, 80%, 85%, 90%, or 95% less than the effective concentration for terbinafine alone and/or the MIC for terbinafine or a pharmaceutically acceptable salt thereof alone as determined for a fungus. In some embodiments, the concentration of terbinafine or a pharmaceutically acceptable salt thereof that is provided and/or delivered to the skin and/or nail of a subject may be at least 1.5-fold (e.g., 2, 2.5, 3, 3.5, 4, 4.5, 5, 5.5, or 6-fold) less than the effective concentration for terbinafine alone and/or the MIC for terbinafine or a pharmaceutically acceptable salt thereof alone as determined for a fungus.

In some embodiments, a combination and/or method of the present invention provides and/or delivers terbinafine or a pharmaceutically acceptable salt thereof at a dose of less than 250 mg per day to a subject. In certain embodiments, a combination and/or method of the present invention provides and/or delivers terbinafine or a pharmaceutically acceptable salt thereof at a dose of less than 250, 240, 230, 220, 210, 200, 190, 180, 170, 160, 150, 140, 130, 120, 110, 100, 90, 80, 70, 60, 50, 40, or 30 mg per day or less.

In some embodiments, a combination and/or method of the present invention provides and/or delivers to a subject an active ingredient (e.g., terbinafine or a pharmaceutically acceptable salt thereof and/or a NO source) at a concentration that is less than a concentration for the active ingredient alone that provides a 3 log microbial kill in a given period of time for a fungus, such as, for example, *T. rubrum*. In some embodiments, the 3 log microbial kill may be in 120 minutes (i.e., MBC120), 3 hours or more, such as, for example, 4, 5, 6, 7, 8, 9, 10, 11, 12, 13, 14, 15, 16, 17, 18, 19, 20, 21, 22, 23, 24 hours or more. A $Log_{10}$ reduction attributable to each active ingredient concentration at each timed exposure is calculated as follows:

$Log_{10}$ reduction=$Log_{10}$, Average (NC)-$Log_{10}$ Average ($P_{EX}$), where NC=Numbers Control Population (CFU/mL)

$P_{EX}$=Post-Exposure Population (CFU/mL)

In some embodiments, a combination and/or method of the present invention provides a fractional bactericidal concentration (FBC) of 0.5 or less. The FBC is determined by identifying the minimum active ingredient concentration that resulted in a three log reduction in the post exposure population (vs. numbers control population) after 24 hours of exposure.

In some embodiments, terbinafine or a pharmaceutically acceptable salt thereof and/or a NO source are administered at a sub-bactericidal concentration. A sub-bactericidal concentration is a concentration of an active ingredient that does not attain a 3-log reduction in bacterial numbers in an in vitro time-kill assay, typically evaluated after 24 hours of challenge with the active ingredient.

Provided according to some embodiments of the present invention is a method of treating and/or preventing a fungal infection in a subject. In some embodiments, a method of treating and/or preventing a fungal infection in a subject may comprise administering terbinafine or a pharmaceutically acceptable salt thereof to the subject; and administering a NO source to the subject. In some embodiments, a method of the present invention may comprise administering a combination (i.e., a fixed combination and/or a non-fixed combination) to the subject.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom associated with a fungal infection is achieved and/or there is a delay in the progression of the fungal infection and/or condition. In some embodiments, the severity of a fungal infection (e.g., a fungal infection caused by T. rubrum) may be reduced in a subject compared to the severity of the fungal infection in the absence of a method of the present invention. In certain embodiments, a method of the present invention treats a fungal infection in a subject, such as a fungal infection that has affected the skin and/or nail of the subject. In some embodiments, a method of the present invention may treat a fungal infection by eliminating and/or reducing the size and/or appearance of at least one clinical symptom associated with the fungal infection (e.g., a disfiguration, discoloration, and/or benign lesion such as a scaly patch). In some embodiments, a method of the present invention may treat a fungal infection by eliminating at least one clinical symptom associated with the fungal infection for a given period of time (e.g., 1, 2, 3, 4, 5, or 6 day(s), or 1, 2, 3, 4, or more weeks, or 1, 2, 3, 4, 5, 6, or more months, etc.).

In some embodiments, terbinafine or a pharmaceutically acceptable salt thereof, a NO source, and/or a combination of the present invention may be administered in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount may be achieved by administering an additive or synergistic combination of the present invention. In some embodiments, administration of a combination of the present invention does not produce systemic effects from the administration of nitric oxide, such as, for example, in a treatment effective amount.

The terms "prevent," "preventing" and "prevention" (and grammatical variations thereof) refer to avoidance, reduction and/or delay of the onset of a fungal infection and/or a clinical symptom associated therewith in a subject and/or a reduction in the severity of the onset of the fungal infection and/or clinical symptom relative to what would occur in the absence of a method of the present invention. The prevention can be complete, e.g., the total absence of the fungal infection and/or clinical symptom. The prevention can also be partial, such that the occurrence of the fungal infection and/or clinical symptom in the subject and/or the severity of onset is less than what would occur in the absence of a method of the present invention. In certain embodiments, a method of the present invention prevents a fungal infection in a subject, such as a fungal infection that can affect the skin and/or nail of the subject.

In some embodiments, terbinafine or a pharmaceutically acceptable salt thereof, a NO source, and/or a combination of the present invention may be administered in a prevention effective amount. A "prevention effective" amount as used herein is an amount that is sufficient to prevent (as defined herein) the fungal infection and/or clinical symptom in the subject. Those skilled in the art will appreciate that the level of prevention need not be complete, as long as some benefit is provided to the subject. In some embodiments, a prevention effective amount may be achieved by administering an additive or synergistic combination of the present invention. In some embodiments, administration of a combination of the present invention does not produce systemic effects from the administration of nitric oxide, such as, for example, in a prevention effective amount.

Terbinafine or a pharmaceutically acceptable salt thereof, a NO source, and/or a combination of the present invention may be administered to a subject using any method known to those of skill in the art. As described above, a combination may be a fixed combination or a non-fixed combination that may be administered to a subject. In some embodiments, terbinafine or a pharmaceutically acceptable salt thereof and a NO source may be administered by the same route of delivery (e.g., both in a form for topical administration) or by different routes of delivery (e.g., one in a form for oral administration and one in a form for topical administration).

The present invention finds use in both veterinary and medical applications. Suitable subjects of the present invention include, but are not limited to avians and mammals. The term "avian" as used herein includes, but is not limited to, chickens, ducks, geese, quail, turkeys, pheasants, parrots, parakeets, macaws, cockatiels, canaries, and finches. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), etc. In some embodiments of the present invention, the subject is a mammal and in certain embodiments the subject is a human. Human subjects include both males and females and subjects of all ages including fetal, neonatal, infant, juvenile, adolescent, adult, and geriatric subjects.

The methods of the present invention may also be carried out on animal subjects, particularly mammalian subjects such as mice, rats, dogs, cats, livestock and horses for veterinary purposes and/or for drug screening and drug development purposes.

In some embodiments, the subject is "in need of" or "in need thereof" a method of the present invention, for example, the subject is in an at-risk population (e.g. the subject may be at-risk for or more susceptible to a fungal infection), the subject has findings typically associated with a fungal infection, and/or the subject has a fungal infection. In some embodiments, a subject in need thereof has a fungal infection and/or a clinical sign or symptom associated therewith that may be treated with a method of the present invention. The present invention may be particularly suitable for children, adolescents, adults, and/or geriatric subjects.

In some embodiments, a combination (e.g., a fixed combination or at least one entity of a non-fixed combination) may be topically administered to a subject. A combination of the present invention may be administered and/or applied topically to any portion of a subject's skin, including mucosa, and/or a nail of a subject. For example, a combination may be topically administered to a subject's hand, finger, foot, toe, arm, leg, trunk, anus, genitals, face, a mucous membrane (including a body cavity), nail (including the skin surrounding and/or under the nail), etc. In some embodiments, a combination of the present invention may be topically administered to at least a portion of a subject's hand, finger, foot, toe, and/or nail (e.g., fingernail and/or toenail).

Example fungal infections include, but are not limited to onychomycosis, tinea capitis, cutaneous candidiasis, tinea corporis, tinea cruris, tinea pedis, and any combination thereof. In some embodiments, a fungal infection may be caused by a dermatophyte, such as, for example, *T. rubrum* and/or *Trichophyton mentagrophytes*.

In some embodiments, a method of the present invention may provide a decrease or reduction in at least one clinical symptom associated with a fungal infection (e.g., a reduction in the size and/or appearance of a benign lesion) in less time than compared to treatment with terbinafine or a pharmaceutically acceptable salt thereof or a NO source alone. For example, a subject may see a decrease or reduction in at least one clinical symptom associated with a fungal infection within 1, 2, 3, 4, 5, 6, 7, 8, 9, 10, 11, 12, 13, or more day(s) and/or week(s).

In some embodiments, a method of the present invention may prevent and/or reduce the appearance and/or size of a benign lesion. Exemplary benign lesions include, but are not limited to, lesions caused by *T. rubrum*, such as, for example, scaly patches and red and/or brown lesions (e.g., those associated with jock itch). A method of the present invention may reduce the appearance and/or size of a benign lesion by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the appearance and/or size of a benign lesion prior to administering of a combination of the present invention. The appearance of the benign lesion may be evaluated visually, such as, but not limited to, by the subject and/or a physician. The size of the benign lesion may be determined using methods known to those of skill in the art.

A method of the present invention may reduce the number of benign lesions by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the number of benign lesions prior to administering of a combination of the present invention. The number of benign lesions may be evaluated visually, such as, but not limited to, by the subject and/or a physician. The number of benign lesions may be determined using methods known to those of skill in the art.

A method of the present invention may decrease the rate of recurrence of a fungal infection in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the rate of recurrence of the fungal infection in the absence of administering of a combination of the present invention (e.g., compared to administration of terbinafine or a pharmaceutically acceptable salt thereof or a NO source alone). The rate of recurrence may be determined using methods known to those of skill in the art. For example, after a treatment of a fungal infection, reinfection may be determined after a given period of time to determine the rate of recurrence.

The present invention is explained in greater detail in the following non-limiting Examples.

EXAMPLES

Example 1

The purpose of this study was to evaluate the synergistic in vitro interactions of one drug pair when challenged with *Tricophyton rubrum* (ATCC #28188).

A minimum inhibitory concentration (MIC) evaluation was performed for each test material versus *T. rubrum* using modifications of the Macrodilution Broth Method outlined in the CLSI (clinical laboratory standards institute) Document M07-A9: *Methods for dilution antimicrobial susceptibility tests for bacteria that grow aerobically*, $9^{th}$ edition. The test materials were terbinafine hydrochloride and Nitricil™ NVN1, which is a NO-releasing diazeniumdiolate-functionalized co-condensed silica from Novan, Inc.

The challenge strain of *T. rubrum* was exposed to a series of doubling dilutions of each test material. Following a 1-4 day incubation period, the MIC evaluation was performed in duplicate to evaluate the synergistic properties of 2 test materials.

An initial population of *T. rubrum* was prepared containing approximately $10^3$ CFU (colony forming units)/mL in appropriate fungal growth media (RPMI). This initial population density was precisely determined by preparing ten-fold dilutions and plating them on the appropriate solid fungal growth media for colony enumeration. These plates were incubated for 5-7 days until sufficient growth was observed. Following incubation, the colonies were manually counted to determine the precise number of colonies present in the initial population.

Testing Procedure:

Phase I—MIC Evaluation of Individual Test Materials

For Nitricil™ NVN1, the appropriate amount of product for each dilution (32, 16, 8, 4, 2, 1, 0.5, 0.125, and 0.063 mg/ml) was weighed out and added to the appropriate volume of fungal growth media. The tube and solution was mixed thoroughly using a vortex mixer.

As soon as the Nitricil™ NVN1concentration was thoroughly dissolved, an aliquot of the dilution was added to a tube containing the challenge *T. rubrum* suspension containing approximately $1\times10^3$ CFU/mL. This resulted in the final test product concentrations of: 16, 8, 4, 2, 1, 0.5, 0.125, 0.063, and 0.032 mg/mL. The final concentration of the *T. rubrum* population per tube was approximately $5\times10^2$ CFU/mL.

For terbinafine hydrochloride, prior to testing a stock solution of 250 µg/mL was made using DMSO. The stock solution was dispensed into small containers and stored appropriately prior to use in testing.

The terbinafine hydrochloride stock solution was diluted into fungal growth media to achieve a solution containing 3.0 µg/mL. Using fungal growth media, serial two-fold dilutions were prepared resulting in final test material concentrations. The final terbinafine hydrochloride test production concentrations were: 3.0, 1.5, 0.75, 0.375, 0.188, 0.094, 0.047, 0.024, 0.012, and 0.006 µg/mL.

Terbinafine hydrochloride material dilutions and the *T. rubrum* challenge suspension was mixed in a 1:1 ratio resulting in a final concentration of the *T. rubrum* population per tube of approximately $5\times10^2$ CFU/mL and terbinafine hydrochloride test article concentrations of: 0.5, 0.75, 0.375, 0.188, 0.094, 0.047, 0.024, 0.012, 0.006, and 0.003 µg/mL.

The challenge suspension/product dilution tubes and all appropriate controls were incubated at 35° C. for 1-4 days until sufficient fungal growth was apparent in the positive control. When good bacterial growth was observed in the positive control, the MIC results were determined.

Determination of Single Drug MIC Results:

The tubes were visually assessed on the basis of turbidity in order to determine fungal growth.

The minimum inhibitory concentration (MIC) of each test material vs. *T. rubrum* was recorded as the lowest concentration of test material that completely inhibits the growth of the fungal species, as determined by the absence of hyphae detected by the unaided eye.

Phase II—Two Test Materials-Interactions

The MIC value of each test material (i.e., Nitricil™ NVN1 and terbinafine hydrochloride) determined in Phase I were used for the beginning point of the checkerboard assay.

Two test material concentrations above and four test materials concentrations below the MIC value (previously determined) were assessed. A series of 1:2 dilutions of each test material were prepared in order to target the dilutions necessary for the checkboard assay performed in duplicate.

Test material prepared for the checkerboard assay was dispensed into test tubes. Each dilution was dispensed into a row or column of eight (one test material decreasing in concentration along x-axis, and the other test material decreasing in concentration along y-axis). The last row of each axis served as the positive control completing the 8×8 grid. The positive control was inoculated with the *T. rubrum* challenge suspension in fungal growth media with no test material.

Following incubation, the tubes were examined for the growth of the fungal species as determined visually via the basis of turbidity.

The minimum inhibitory concentration (MIC) of each test material vs. *T. rubrum* was recorded as the lowest concentration of test material that completely inhibits the growth of the fungal species, as detected by the unaided eye.

Calculations for Checkerboard Assay:

A fractional inhibitory index (FIX) was used to interpret the results of the two-material interaction series: ΣFIX=FIC A+FIC B, where:

$$FIC\ A = \frac{MIC\ of\ drug\ A\ in\ the\ combination}{MIC\ of\ drug\ A\ alone}$$

$$FIC\ B = \frac{MIC\ of\ drug\ B\ in\ the\ combination}{MIC\ of\ drug\ B\ alone}$$

The ΣFIX for the two material interaction was interpreted as follows:

SYN=Synergy was considered an ΣFIX≤0.5
ADD=Additive was considered an ΣFIX>0.5 but ≤4.0
ANT=Antagonistic was considered an ΣFIX>4.0

The results of the Phase I: Minimum Inhibitory Concentration (MIC) Evaluation for each test materials are provided in Table 1.

The results of the Phase II: Fractional Inhibitory Concentration (FIC) Values for Two Test Material Interactions are provided in Table 2.

TABLE 2

FIX values for *T. rubrum* based on the combination of terbinafine hydrochloride and Nitricil ™ NVN1.

| Microorganism | Replicate # | Test Material #1 and #2 (Nitricil ™ NVN1 & Terbinafine hydrochloride) |
| --- | --- | --- |
| *Tricophyton rubrum* (ATCC # 28188) | 1 | SYN (FIX = 0.313) |
| | 2 | SYN (FIX = 0.313) |

Figure 1:
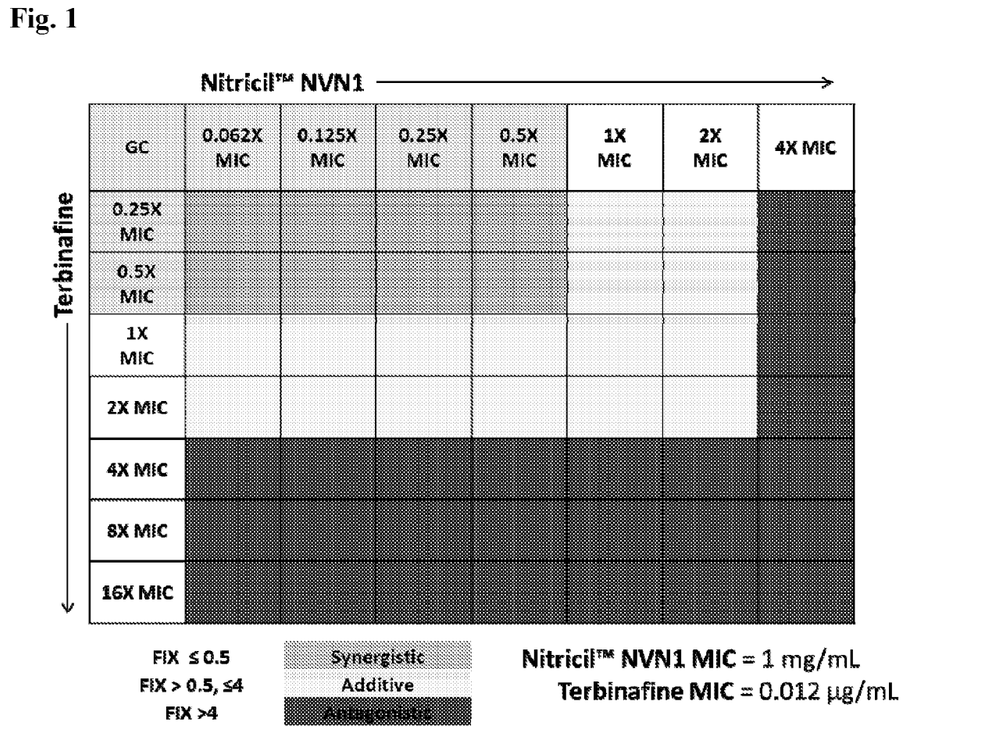
FIG. 1 is an image of the results from an in vitro checkerboard assay investigating the effect of Nitricil™ NVN1 and terbinafine hydrochloride on *T. rubrum*.

The results from the in vitro checkerboard assay are shown in FIG. 1. The combination of Nitricil™ NVN1 and terbinafine hydrochloride provided a MIC value for Nitricil™ NVN1 that was 4-fold less than the MIC value for Nitricil™ NVN1 alone and for terbinafine hydrochloride that was 2-fold less than the MIC value for terbinafine hydrochloride alone. Thus, the combination demonstrated a synergistic effect. As shown in FIG. 1, a synergistic effect was achieved with 0.062× MIC, 0.125× MIC, 0.25× MIC, and 0.5× MIC of Nitricil™ NVN1 and 0.25× MIC or 0.5× MIC of terbinafine hydrochloride.

Example 2

In vitro *T. rubrum* time-kill assays were performed. For the in vitro time-kill evaluation, four concentrations of each test product were prepared in 100 mM Tris, pH 7.5-7.7. A 10 mL aliquore of each test product concentration was inoculated with a 0.1 mL aliquot of the *T. rubrum* challenge suspension containing approximately $10^9$ CFU/mL. The *T. rubrum* challenge suspension was exposed to each concentration of test product for 4 and 24 hours. A 0.1 mL aliquot of the *T. rubrum* challenge suspension was inoculated into a test tube containing 10 mL of 0.9% sodium chloride solution and exposed for 24 hours to serve as a numbers control. After each exposure time had elapsed, a 1.0 mL aliquot was transferred from the test product/inoculum into a test tube containing 9.0 mL Butterfield's Phosphate Buffer solution with product neutralizers and mixed thoroughly using a vortex mixer. Ten-fold dilutions were prepared in neutralizing solution and mixed thoroughly between dilutions. 1.0 mL and 0.1 mL aliquots of each dilution were plated, in duplicate, using Emmon's Sabourad Dextrose Agar with product neutralizers. The bacterial plates were incubated at 25° C.±2° C. for five to seven days until sufficient fungal growth was observed. Following incubation, the colonies were counted manually using a hand-tally counter. The average CFU/mL and $Log_{10}$ average CFU/mL of the average of the duplicate plate counts for initial population and

TABLE 1

MIC for *T. rubrum* for each test material alone

Figure 2:
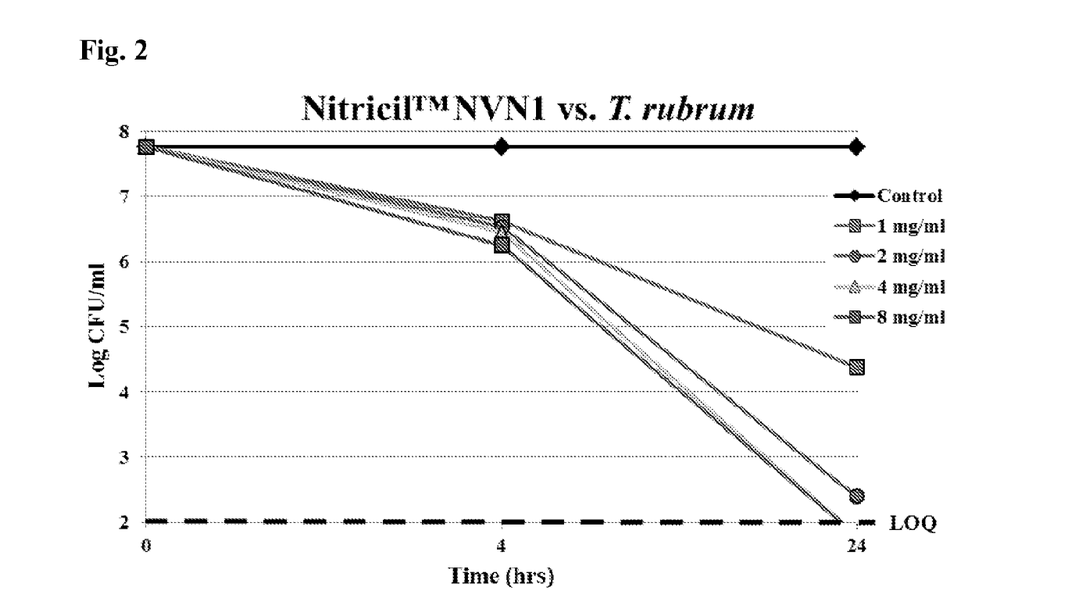
FIG. 2 is a graph showing the results of an in vitro *T. rubrum* time-kill assay with Nitricil™ NVN1.
Figure 3:
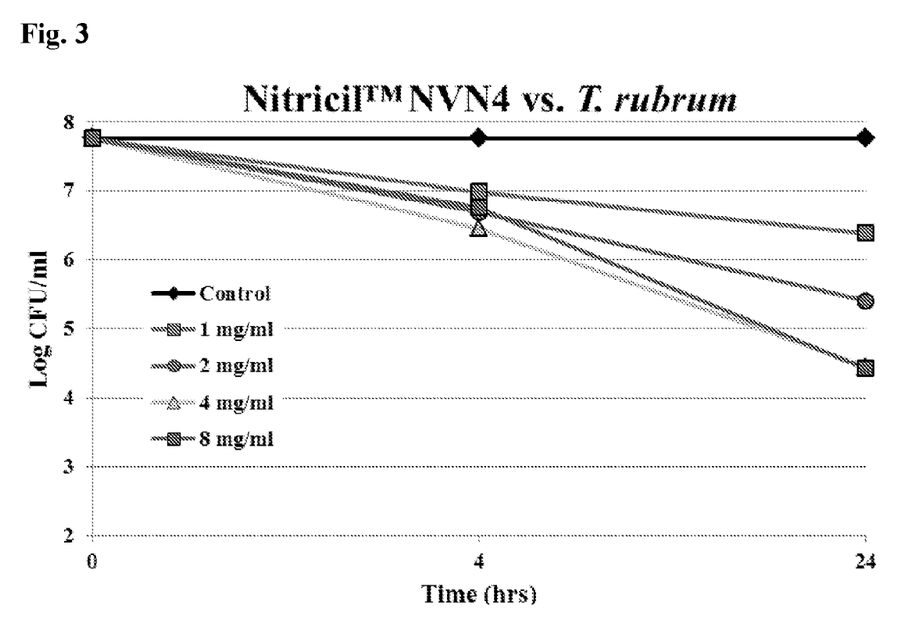
FIG. 3 is a graph showing the results of an in vitro *T. rubrum* time-kill assay with Nitricil™ NVN4.
Figure 4:
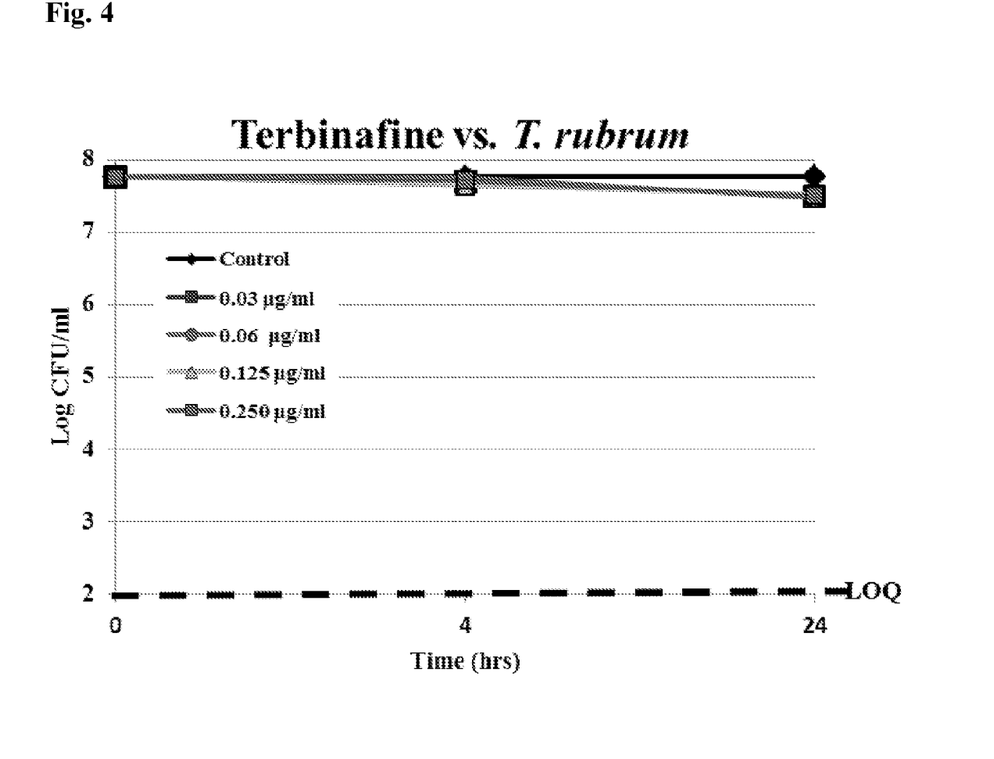
FIG. 4 is a graph showing the results of an in vitro *T. rubrum* time-kill assay with terbinafine hydrochloride.

| Microorganism | Inoculum Population (per tube; CFU/mL) | Test Materials | Minimum Inhibitory Concentration (MIC) (as product concentration) |
| --- | --- | --- | --- |
| *Tricophyton rubrum* (ATCC # 28188) | $1.775 \times 10^3$ | Nitricil ™ NVN1 | 1 mg/mL |
| | | Terbinafine hydrochloride | 0.012 µg/mL | numbers control for the challenge suspension, and post-exposure populations ($P_{EX}$) versus each test product concentration at each exposure time were calculated as follows:

$$CFU/ml = C_i \times 10^{-D}$$

$$Log_{10} Average = log_{10}(C_i \times 10^{-D})$$

where $C_i$=Average colony counts of the plates counted
D=Dilution factor of the plates counted The results of the in vitro *T. rubrum* time-kill assay with Nitricil™ NVN1 are shown in FIG. 2. The results of the in vitro *T. rubrum* time-kill assay with Nitricil™ NVN4 are shown in FIG. 3. The results of the in vitro *T. rubrum* time-kill assay with terbinafine hydrochloride are shown in FIG. 4.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

What is claimed is:

1. A method of treating and/or preventing a fungal infection in a subject, the method comprising:
   administering terbinafine or a pharmaceutically acceptable salt thereof to the subject; and
   administering a NO source to the subject, thereby treating and/or preventing the fungal infection in the subject,
   wherein the NO source is a N-diazeniumdiolate-functionalized macromolecule, and
   wherein terbinafine or a pharmaceutically acceptable salt thereof and the NO source are each administered to the subject at a dose that achieves a synergistic effect.

2. The method of claim 1, wherein administering the NO source to the subject comprises increasing a level of nitric oxide at a given site on and/or in a subject.

3. The method of claim 2, wherein the given site comprises skin and/or a nail of the subject where the fungal infection is present.

4. The method of claim 1, wherein the N-diazeniumdiolate-functionalized macromolecule is a N-diazeniumdiolate co-condensed polysiloxane macromolecule.

5. The method of claim 1, wherein administering the NO source to the subject further comprises releasing nitric oxide from the NO source by exposure to light and/or an electrical current.

6. The method of claim 1, wherein administering terbinafine or the pharmaceutically acceptable salt thereof to the subject comprises administering terbinafine or the pharmaceutically acceptable salt thereof at a dose of less than 250 mg per day.

7. The method of claim 1, wherein the NO source delivers a dose of nitric oxide to the subject that is at least 20% less than the concentration effective to inhibit fungi growth and/or kill fungi for the NO source alone.

8. The method of claim 1, wherein terbinafine or a pharmaceutically acceptable salt thereof is administered at a concentration that is less than a concentration for terbinafine or the pharmaceutically acceptable salt thereof alone that provides a 3 log microbial kill for the fungi in 4 hours or 24 hours and the NO source is administered at a concentration that is less than a concentration for the NO source alone that provides a 3 log microbial kill for the fungi in 4 hours or 24 hours.

9. The method of claim 1, wherein terbinafine or a pharmaceutically acceptable salt thereof and the NO source are each administered at a concentration that provides a greater than or equal to 2 $log_i c$ (CFU/mL) decrease in fungi compared to administration of terbinafine or a pharmaceutically acceptable salt thereof or the NO source alone.

10. The method of claim 1, wherein terbinafine or a pharmaceutically acceptable salt thereof and the NO source are each administered at a sub-microbial bactericidal concentration for the fungi.

11. The method of claim 1, wherein terbinafine or a pharmaceutically acceptable salt thereof is administered at a concentration that is less than a concentration for terbinafine or the pharmaceutically acceptable salt thereof alone that provides a 3 log microbial kill for the fungi in 4 hours or 24 hours.

12. The method of claim 1, wherein the NO source is administered at a concentration that is less than a concentration for the NO source alone that provides a 3 log microbial kill for the fungi in 4 hours or 24 hours.

13. The method of claim 1, wherein administering terbinafine or the pharmaceutically acceptable salt thereof to the subject comprises administering terbinafine or the pharmaceutically acceptable salt thereof at a dose of less than 200 mg per day.

14. The method of claim 1, wherein terbinafine or a pharmaceutically acceptable salt thereof and the NO source are simultaneously administered to the subject.

15. The method of claim 1, wherein terbinafine or a pharmaceutically acceptable salt thereof and the NO source are sequentially administered to the subject in any order.

16. The method of claim 1, wherein terbinafine or a pharmaceutically acceptable salt thereof and the NO source are separately administered to the subject.

17. The method of claim 1, wherein terbinafine or a pharmaceutically acceptable salt thereof and the NO source are in a fixed combination that is administered to the subject.

* * * * *

UNITED STATES PATENT AND TRADEMARK OFFICE
CERTIFICATE OF CORRECTION

PATENT NO. : 10,849,864 B2
APPLICATION NO. : 15/747981
DATED : December 1, 2020
INVENTOR(S) : McHale et al.

It is certified that error appears in the above-identified patent and that said Letters Patent is hereby corrected as shown below:

In the Specification

Column 3, Line 16: Please correct "20%" to read -- ±20% --

Column 3, Line 16: Please correct "+5%" to read -- ±5% --

Column 12, Line 8: Please correct "20 μM" to read -- 20 μm --

Column 21, Line 4: Please correct "*CFU/ml*" to read -- *CFU/mL* --

In the Claims

Column 22, Line 18, Claim 9: Please correct "2 $\log_i c$" to read -- 2 $\log_{10}$ --

Column 22, Lines 23-24, Claim 10: Please correct "sub-microbial bactericidal concentration" to read -- sub-microbial concentration --

Signed and Sealed this
Third Day of August, 2021

Drew Hirshfeld
*Performing the Functions and Duties of the
Under Secretary of Commerce for Intellectual Property and
Director of the United States Patent and Trademark Office*